United States Patent [19]

Maeda

[11] 4,406,167
[45] Sep. 27, 1983

[54] ULTRASONIC FLAW-DETECTION METHOD FOR AUSTENITIC ALLOY STEEL LONGITUDINALLY WELDED PIPE AND TUBING

[75] Inventor: Taro Maeda, Osaka, Japan

[73] Assignee: Nisshin Steel Co., Ltd., Tokyo, Japan

[21] Appl. No.: 250,948

[22] Filed: Apr. 6, 1981

[30] Foreign Application Priority Data

Apr. 10, 1980 [JP] Japan .................................. 55-46220

[51] Int. Cl.³ ............................................. G01N 29/04
[52] U.S. Cl. ........................................ 73/622; 73/629; 73/632
[58] Field of Search ........................ 73/622, 629, 632; 310/336

[56] References Cited

U.S. PATENT DOCUMENTS

| | | | |
|---|---|---|---|
| 3,299,696 | 1/1967 | Dickinson | 73/622 |
| 3,868,847 | 3/1975 | Gunkel | 73/622 |
| 4,058,000 | 11/1977 | Ries et al. | 73/629 |
| 4,065,960 | 1/1978 | Grabendorfer et al. | 73/622 |
| 4,295,375 | 10/1981 | Ganglbauer et al. | 73/627 |

FOREIGN PATENT DOCUMENTS 2027199 2/1980 United Kingdom .................. 73/622

*Primary Examiner*—Howard A. Birmiel
*Attorney, Agent, or Firm*—Fitzpatrick, Cella, Harper & Scinto

[57] ABSTRACT

Ultrasonic flaw-detection method for austenitic alloy steel longitudinally welded pipe or tubing adopts shear wave angle method using a broad-band high-damping and non-resonance type transducer.

4 Claims, 9 Drawing Figures

ULTRASONIC FLAW-DETECTION METHOD FOR AUSTENITIC ALLOY STEEL LONGITUDINALLY WELDED PIPE AND TUBING

This invention concerns ultrasonic flaw-detection method for longitudinal welds of austenitic alloy steel electrically welded pipe and tubing.

Ultrasonic flaw-detection of austenitic alloy steel welds has been regarded as difficult or occasionally impossible. Such a situation is caused by coarse grained and elastically anisotropic dendritic crystallographical structure of weld metal of austenitic alloy steel which tends to attenuate the ultrasonic beam, evolve coherent structural noise called forest echo or grass echo due to acoustic beam scattering at dendritic grain boundaries with the equivalent level of echo height as flaw signals, cause beam steering phenomenon and cause beam refraction at bond of welds and base metal. As one of the countermeasures to solve such difficulties one may adopt the longitudinal wave angle method due to recent technological development. When the longitudinal wave angle method is adopted, however, shear waves propagate in test material at smaller refraction angle and with slower acoustic velocity than those of longitudinal waves according to Snell's law and besides the longitudinal wave itself loses most of its own energy when it is reflected at the inside reflecting point of a half skip distance due to the mode conversion phenomenon, so that the flaw reflection echoes other than those caused by flaws lying on the longitudinal wave propagating path between incident points, and a half skip distance point can not be distinguished from flaw echoes caused by shear waves.

It is an object of this invention to eliminate the disadvantages noted above, and provide an improved ultrasonic flaw-detection method for austenitic alloy steel longitudinally welded and tubing.

It is a further object of this invention to use larger range of beam propagating path length i.e. that covering the range between incident point and at least one and a half skip distance points.

It is also an object of this invention to simplify the technique so that the ultrasonic flaw-detection may be carried out automatically.

According to my invention, in order to attain the above objects, I employ customary shear wave angle method which utilizes an incidence angle larger than the critical one which makes the refraction angle of the longitudinal wave larger than 90 degrees.

It is another object of this invention to provide an ultrasonic flaw-detection method, especially suitable for austenitic alloy steel longitudinally welded pipe or tubing which has a wall thickness (t) from 0.5 mm to 15 mm, an outer diameter (D) more than 5 mm and a t/D ratio smaller than 20%.

For a complete understanding of this invention, together with an appreciation of this and other objects and advantages, please see the following detailed description as well as the attached drawings, in which.

Figure 5:
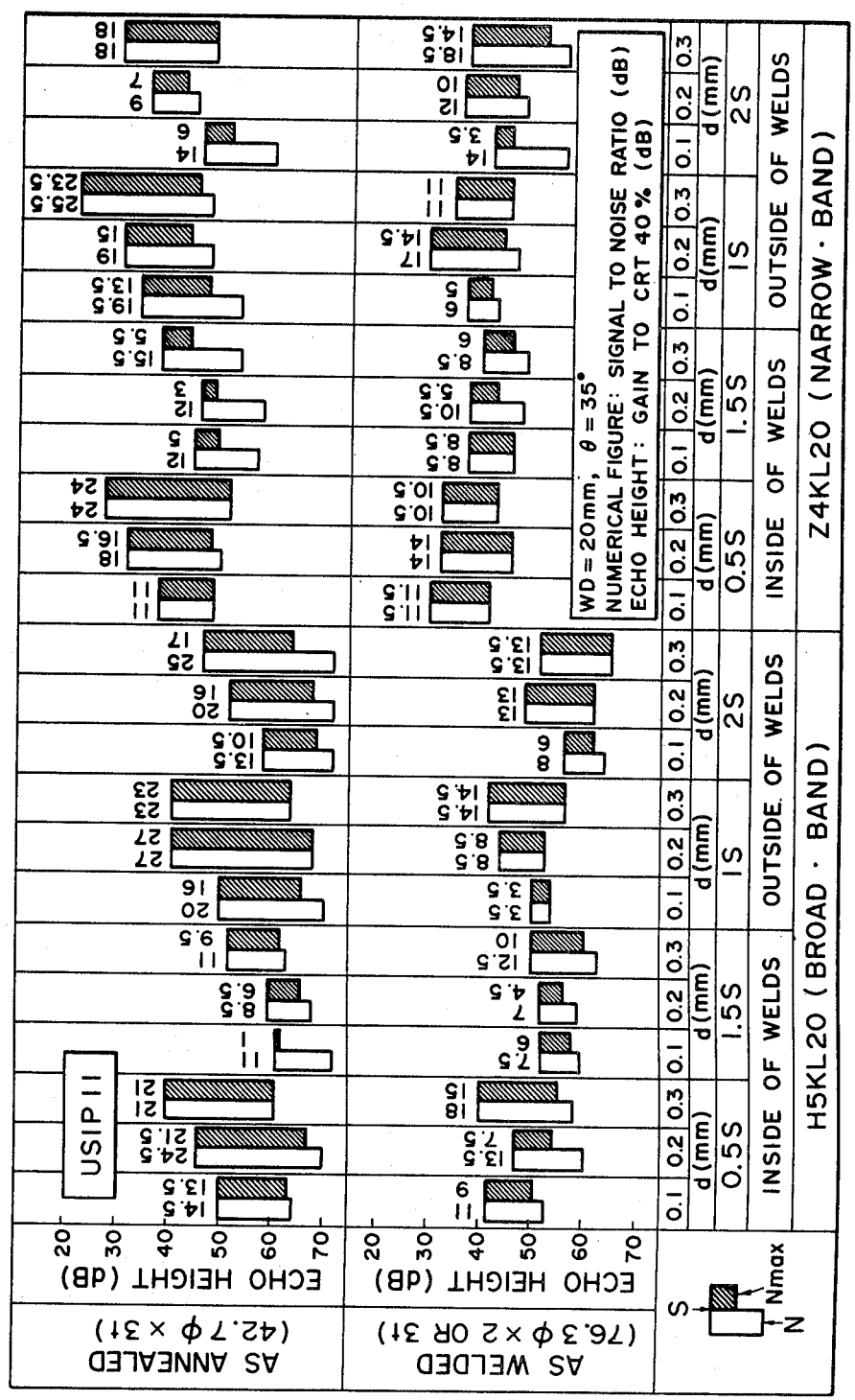
Figure 6:
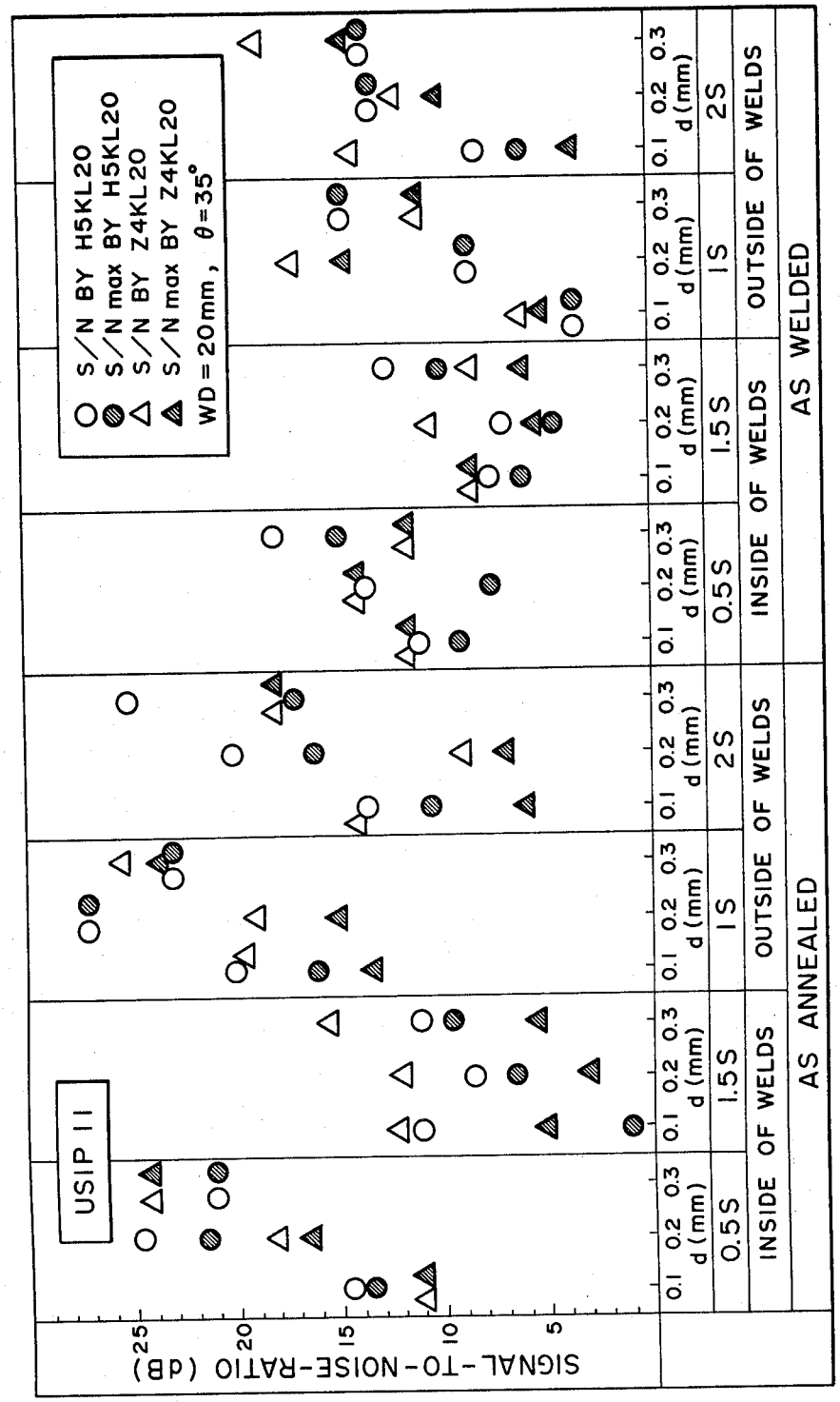

in FIGS. 2A to 4B, notation S represents the surface echo and notation F represents the square notch echo;

FIG. 5 shows a graphical representation of the comparison of stability in ultrasonic static detection of 10 mm longitudinal reference U-notches of austenite stainless steel tubing for broad band and narrow band transducers;

FIG. 6 shows a graphical representation of the comparison of signal-to-noise ratio is ultrasonic static detection of 10 mm longitudinal U-notches of austenitic stainless steel tubing for broad band and narrow band transducers.

In the objective longitudinal welds fabricated by electrical fusion welding, electrical resistance welding or electrical induction welding of the pipe or tubing as described, the cross-sectional dimension is comparatively small and the crystallographic structure is comparatively fine and ordered. In addition, the range of acoustic beam path used in ultrasonic flaw-detection of this invention would be sufficient if it would be two skip distances, at most. Accordingly, in this case, the attenuation of the ultrasonic beam does not become the detrimental factor, so that it is most important to enhance and stabilize the signal-to-noise-ratio by suppressing structural noise.

For this purpose, according to the invention, firstly a line-focusing or point-focusing transducer is preferably adopted to give the practical effect, and more preferably, for all kinds of shear wave angle methods, regardless of various coupling techniques i.e. immersion technique, several kinds of partial immersion techniques or a direct contact method with the use of wedges, a focusing transducer whose focal length gives beam converging at any point between incident point and a half skip length point after propagating some water distance or wedge distance before incidence into the test material may be used.

Even beam focusing alone, as described, brings about some positive effect on improvement of the signal-to-noise ratio, however, this has been also adopted for the techniques based on the pre-described longitudinal wave angle method. The shear wave angle method itself has been also commonly utilized in ultrasonic flaw detection for ordinary steel weldments. But the transducers commonly used in the conventional shear wave angle method have an oscillator made of lead zircum titanate ceramic (Z type) or barium titanate ceramic (B type), and can not improve the signal-to-noise-ratio for the objective materials of this invention, even if focusing facilities are added, because of a narrow band width of the frequency spectrum around the nominal frequency of their own i.e. because they are narrow-band type transducers. Namely even if narrow-band type focusing transducers were employed, the detectability of reference artificial flaws made in the midst of welds of austenitic alloy longitudinally welded pipe and tubing, the objective materials of this invention, which are used for calibration of flaw-detecting sensitivity and setting the natural flaw rejection level, can not be improved as in the base metal of austenitic alloy steel, austenitic alloy steel seamless tubing and in the base metal and weldments of ferritic alloy steel. In this case, the reference artificial flaws are longitudinal or transverse notches of square-, U- or V-shape in cross-section on the outer and inner surface of the longitudinal welds made by the spark-erosion method, those notches having depth of 0.1 mm to 20% of the wall thickness, a width of 0.15 mm to twice of the depth and a length of 5 mm to 25 mm. The reference artificial flaw may be holes radially pieced or drilled which have 1.6 mm or 3.2 mm diameter. The detectability of those reference artificial flaws in the welds of austenitic alloy steel longitudinally welded pipe and tubing is not improved sufficiently by the use of the narrow-band type focusing transducers, as mentioned below. Concretely speaking, the detectability afforded by the narrow-band type focusing transducers is no more than what is described in the following: In the non-annealed (as welded) welds the signal-to-noise-ratio is so insufficient that automatic flaw detection is impossible and even in the annealed (solution-treated) welds the signal-to-noise-ratio is somewhat raised but still unstable, and a static signal-to-noise-ratio more than 10 dB which is regarded as the necessary lower limit to accomplish automatic dynamical examination, would not be expected for a whole range of fluctuation of metallographical structure of annealed welds.

Thus, according to this invention, a broad-band high-damping and non-resonance type focusing transducer having an oscillator made of material which can easily afford high-damping and non-resonance characteristics is adopted in order to assure detectability for reference artificial flaws, as above-mentioned, in the welds of austenitic alloy steel longitudinally welded pipe and tubing. Such an oscillator may be made of lead niobate ceramic or lead titanate ceramic. In this way the detectability of reference artificial flaws is assured with sufficient stability and reproducibility for the whole actual fluctuation range of metallographical state of welds. The detectability guarantees an enhanced signal-to-noise-ratio and sufficient flaw-detecting sensitivity, so that it makes it possible, for example, to accomplish high speed inspection by use of a transducer-rotating and tube-translating type installation with examining surface coverage of 100% or more, i.e. over-lapping. Such excellent ultrasonic flaw detectability for welds of austenitic alloy steel which is afforded by the broad-band high-damping and non-resonance type transducer is due to following three main reasons.

The first reason is as follows: It is always easy to send ultrasonic waves with most suitable frequency for the welds of inspected material with sufficient acoustic pressure. Namely in the ultrasonic flaw-detection for welds of austenitic alloy steel there exists suitable ultrasonic frequency determined by the metallographical structure of individual test material which makes it possible substantially to suppress the structural noise and enhance the signal-to-noise-ratio to the maximum extent. On the other hand, the commercially available broad-band type transducers, of which 2, 2.5, 4, 5, 10 MHz or the like nominal frequencies are available, have wide frequency spectrum band width around the nominal frequencies i.e. the central frequencies which includes all of the components of acoustic energy of not less than 3 dB energy drop from the maximum component energy of the frequency spectrum. Accordingly, by choosing the broad-band type transducer of an appropriate nominal frequency, it becomes easy to send the ultrasonic wave component of optimum frequency for the welds of occasional test material and to suppress the structural noise. Thus it is possible practically to suppress the structural noise and enhance the signal-to-noise-ratio effectively.

The second reason is as follows:

Owing to the composite effect of short impulse such as shock wave of the broad-band high-damping and non-resonance type transducer with the beam focusing, the beam-axial-section's ratio of flaw-signal-reflecting-zone versus structural-noise-reverberating-zone can be made maximal at the focal zone of the transducer. Thus the structural noise due to beam scattering at the grain boundary of dendrites can be suppressed to the minimal and thus the signal-to-noise-ratio can be enhanced to a practically higher level.

The third reason is as follows:

Owing to the high resolution due to the short impulse length of the broad-band high-damping and non-resonance type transducer, it becomes possible to separate the flaw echo (F-echo) from the surface echo (S-echo) to the highest possible extent. As the result of that, the length of the initial part of the incident beam path which is covered by S-echo can be made minimal so that the gate range of beam path length which is used for flaw-evaluation can be brought close to the incident point. This brings a favorable effect to raise the flaw-detecting-efficiency combined with the focusing effect and to get a better signal-to-noise-ratio. Concretely describing the above-mentioned situation, the effective result of flaw-detecting by focused beam is expected basically by setting the gate to the range between 0.25 skip-distance and 1 skip-distance for test material of thicker wall-thickness and to the range between 0.75 skip-distance and 1.5 skip-distance even for test material of thinner wall-thickness.

The adoption of the broad-band high-damping and non-resonance type focusing transducer brings about not only the above-mentioned main effects of improving signal-to-noise-ratio resulting from suppression of structural noise but also the following subsidiary effect which is also essential for effective ultrasonic flaw detection, especially for automatic flaw-detecting for longitudinally welded pipe and tubing. The above-mentioned subsidiary effect also comes from high resolution characteristics by shock wave effect. That is based upon the fact that the best separation of flaw-echo (F-echo) from the disturbing echo of internal weld reinforcement of pipe and tubing can be obtained due to short impulse length. Namely, when depending upon the weld reinforcement's height and shape, the height of disturbing echoes of internal weld reinforcement becomes as high as that of the minimum flaw which should be detected, it becomes possible to set a single gate or separated gate if necessary which lies on the beam path which is as short as possible and avoids the disturbing echo of internal weld reinforcement. Concretely describing the above-mentioned situation, the effective result of flaw-detecting by focused beam is expected basically by setting the gate to a couple of ranges of 0.25 skip-distance—0.5 skip-distance and 0.75 skip-distance—1 skip-distance for test material of thickner wall-thickness and to the range of 1 skip-distance—1.5 skip-distance for test material of thinner wall-thickness and, if necessary, by lowering the flow-detecting-sensitivity slightly or occasionally by adjusting the refraction angle. This subsidiary effect can not be expected by the shear wave angle method using customary Z or B type focusing transducers.

By the way, although sufficient effect is obtained by use of a standard receiver which has a narrow-band amplifier when the method according to this invention is applied to practical flaw detection a much better result is obtained if a receiver equipped with an amplifier of the equal frequency band range to what is characteristic of the broad-band transducer used is employed. And the decrease of sensitivity due to short pulse width which is peculiar to broad-band high-damping and non-resonance transducers is in such a degree that it can afford to give sufficient allowance of sensitivity by either amplifier of receiving equipment so that it is always possible to get sufficient overall practical sensitivity.

Owing to the above-mentioned features, the method of this invention can be applied to either item of ultrasonic flaw detection of austenitic alloy steel longitudinally welded pipe and tubing e.g. tubing fabricating mill on line automatic ultrasonic inspection of non-annealed, i.e. as-weled material, off-line automatic ultrasonic inspection of finished material and off-line semi-automatic or manual ultrasonic inspection of both annealed, i.e. solution-treated and non-annealed, i.e. as welded materials. On the other hand, if the conditions which have been described with respect to this invention are not satisfied, it would be impossible to accomplish the objects with sufficient stability and reproducibility in any of the prescribed items of ultrasonic alloy steel longitudinally welded pipe and tubing.

Figure 1:
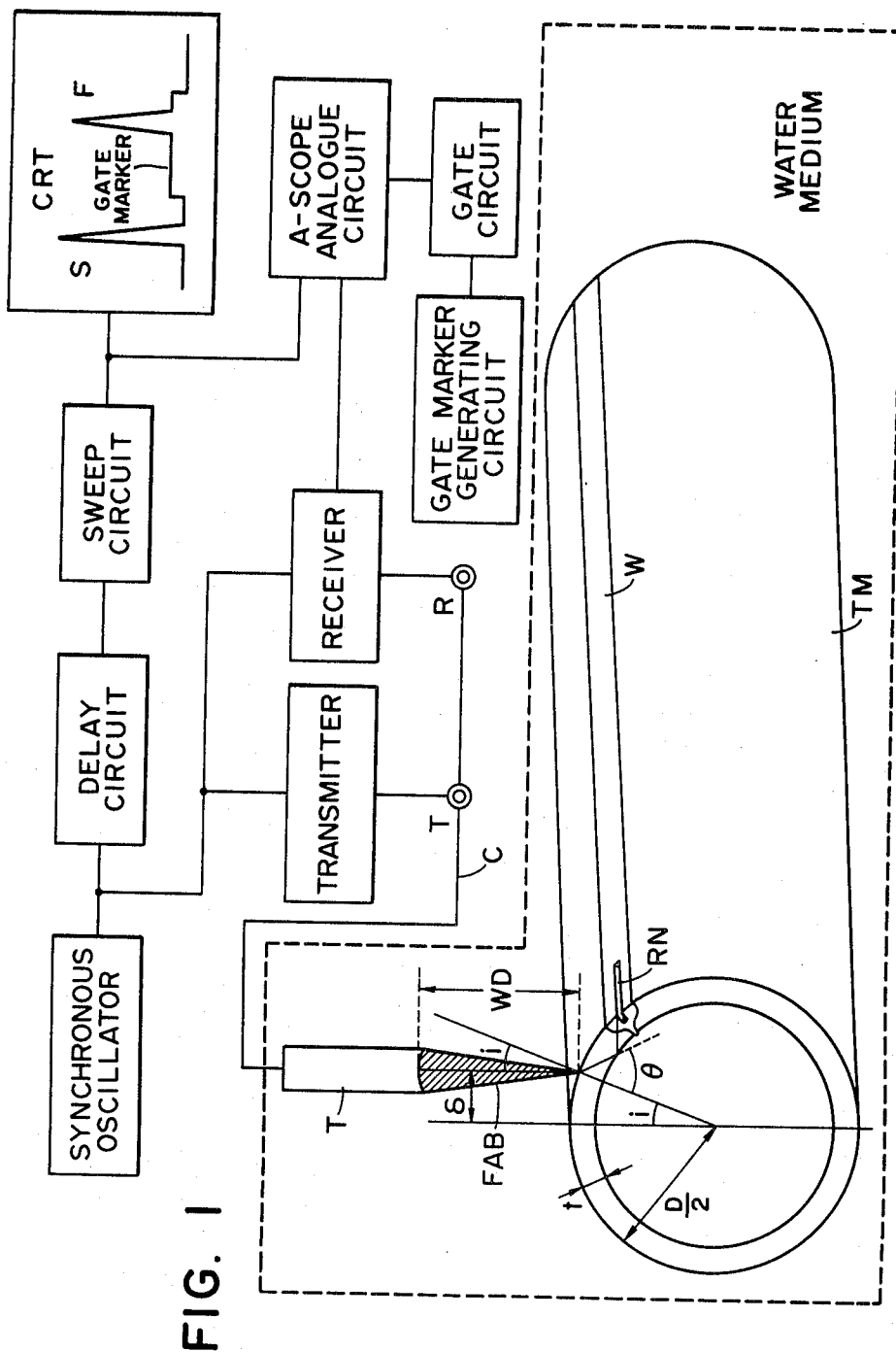
FIG. 1 is a schematic diagram of an ultrasonic flaw detecting system for carrying out the method according to the invention.

FIG. 1 shows schematically a flaw-detecting system for carrying out the inventive method, in which TM is pipe or tubing which is the material to be tested; C is a cable; T is a line-focusing transducer; FAB is a focused acoustic beam; $\delta$ is an off-set distance; WD is a water distance; i is an incident angle; $\theta$ is a refraction angle; D is an outer diameter of the test material; W is welds of the test material; and RLN is a reference longitudinal square notch on the outer surfaae of the test material. The off-set distance $\delta$ is $$\delta = (D/2)\sin i$$

There is the following relation:

$$\sin \theta = \frac{V_L(H_2O)}{V_S(\gamma_{ss})} \sin i$$

where $V_L(H_2O)$ is acoustic velocity of the longitudinal wave in water, and $V_S(\gamma_{ss})$ is acoustic velocity of the shear wave in austenitic stainless steel.

The actual comparative tests were carried out, as described in detail below and the test results are shown in the attached drawings.

COMPARATIVE EXAMPLE 1

Figure 2A:
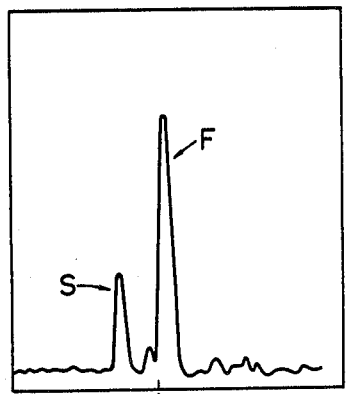
FIGS. 2A and 2B show the A-scope CRT patterns of ultrasonic flaw detection of the comparative example 1.
Figure 2B:
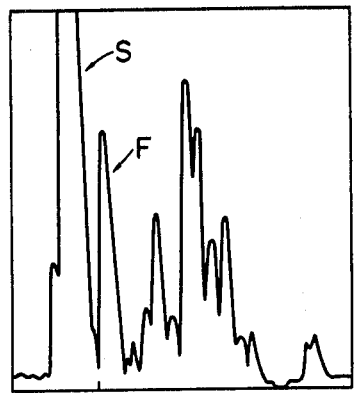

AISI Type 304 austenitic stainless steel longitudinally electric-induction-welded tubing which is of dimension of 60.5 mm$\phi$×2 mmt with cut internal weld reinforcement and non-annealed, i.e. as welded was employed as the test material. The longitudinal square-notch of 0.15 mm depth and 25 mm length spark eroded in the midst of welds on internal surface was ultrasonically examined statically by the in-water-immersion-method. Two kinds of transducers, broad-band high-damping and non-resonance type line-focusing transducer having nominal frequency 5 MHz, Japanese Industrial Standard (abbreviated JIS hereinbelow) 5C10ILF20 (trade name HSKL20 manufactured and sold by KRAUTKRÄMER, and customary narrow-band type non-focusing transducer having nominal frequency 4 MHz, JIS 4Z10I (trade name Z4K manufactured and sold by the same company), were employed. The results obtained by these transducers were compared. The A-scope CRT patterns by those two transducers are shown in FIG. 2A and FIG. 2B. FIG. 2A is the result obtained by 5C10ILF20 and FIG. 2B is that by 4Z10I. The ultrasonic flaw-detecting conditions which gave the above-mentioned A-scope CRT patterns and the values of signal-to-noise-ratio which were measured at the same flaw-detecting arrangements are shown in Table 1.

TABLE 1

| Transducer | 5C10ILF20 | 4Z10I |
| --- | --- | --- |
| Signal-to-noise-ratio (dB) | 20 | 6 |
| Gain-value (dB) | 30 | 22 |
| Refraction angle (degree) | 45 | 45 |
| Ultrasonic equipment | portable | portable |

From the result which is shown in FIGS. 1A and 1B, comparing the flaw-detecting effects are which are given by the broad-band high-damping and non-resonance type line-focusing transducer 5C10ILF20 [FIG. 2A] and the customary narrow-band Z type non-focusing transducer 4Z10I [FIG. 1B], the following evaluation is recognized: The transducers 5C10ILF20 satisfies the aim of this invention, on the other hand the transducer 4Z10I does not accomplish it. And the signal-to-noise-ratio of 6 dB which was given by 4Z10I is so small that the adoption of 4Z10I to automatic flaw detection would be impossible. Signal-to-noise-ratio was shown as the difference of echo height (dB) of the notch signal (S) and noise (N). Echo height was always shown by gain value (dB) adjusted to bring the echo height up to 60% of full scale of the longitudinal axis of the CRT. The noise was measured in sound welds neighbouring the artificial flaw, i.e. square notch-including region at the equal beam path to that of the artificial flaw. Accordingly, the noise level cannot be predicted directly from the CRT pattern of FIG. 2A or 2B. The method of measurement of signal-to-noise-ratio is the same in the comparative example 2 and 3 described below.

COMPARATIVE EXAMPLE 2

Figure 3A:
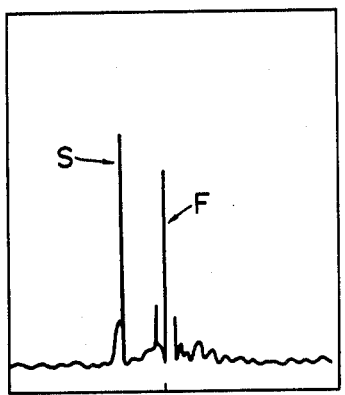
FIGS. 3A and 3B show the A-scope CRT patterns of ultrasonic flaw detection of the comparative example 2.
Figure 3B:
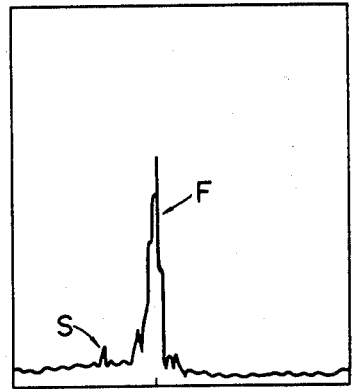

AISI Type 304 austenitic stainless steel longitudinally electric-fusion-welding tubing which is of dimension of 165.2 mm$\phi$×2.8 mmt and non-annealed i.e. as welded, was employed as the test material. The longitudinal square notch of dimension of 5% of weld thickness, i.e. 0.14 mm deep and 25 mm long and spark-eroded in the midst of welds on the outer surface was ultrasonically examined statically by the in-water-immersion-method as in the Example 1. Two kinds of transducers, broad-band high-damping and non-resonance type line-focusing transducer, 5C10ILF20, the same one as used in Example 1, and customary narrow-band type line focusing transducer having nominal frequency 4 MHz, JIS 4B10ILF (trade name Z4KL20 manufactured and sold by KAUTKRÄMER) were employed. The results obtained by these transducers were compared. The A-scope CRT patterns of those two transducers are shown in FIG. 3A and FIG. 3B. FIG. 3A is the result obtained by 5C10ILF20 and FIG. 3B is that by 4B10ILF. The ultrasonic flaw-detecting condition which gave the above illustrated A-scope CRT patterns and the values of signal-to-noise-ratio which were measured at the same flaw-detecting arrangements are shown in Table 2.

TABLE 2

| Transducer | 5C10ILF20 | 4B10ILF |
| --- | --- | --- |
| Signal-to-noise-ratio (dB) | 16 | 8 |
| Gain-value (dB) | 40 | 24 |
| Refraction angle (degree) | 45 | 45 |
| Ultrasonic equipment | portable | portable |

From the result which is shown in FIGS. 3A and 3B, the following evaluation is obtained: The transducer 4B10ILF [FIG. 3B] which does not evolve the surface-echo i.e. S-echo in this case is insufficient to satisfy the aim of this invention from both standpoints of signal-to-noise-ratio and resolutionability. Especially the lower signal-to-noise-ratio of 8 dB suggests that it is impossible to apply this transducer to automatic flaw detection. On the other hand, the broad-band high-damping and non-resonance type line-focusing transducer 5C10ILF20 [FIG. 3B] which concerns this invention, accomplishes completely the object of this invention.

COMPARATIVE EXAMPLE 3

Figure 4A:
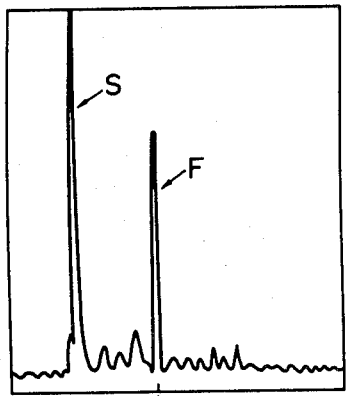
FIGS. 4A and 4B show the comparison A-scope CRT patterns of ultrasonic flaw detection of the comparative example 3.
Figure 4B:
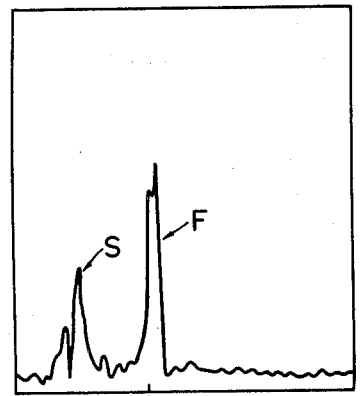

AISI Type 304 austenitic stainless steel longitudinally electric-fusion-welded tubing which is of dimension of 114.3 mm$\phi$×6.0 mmt, with polished internal weld reinforcement and annealed, i.e. solution-treated was employed as the test material. The longitudinal square notch of dimension of 5% of wall thickness i.e. 0.3 mm deep and 25 mm long spark eroded in the midst of welds on the outer surface was ultrasonically examined statically by the in-water-immersion-method as in examples 1 and 2. Transducers employed were exactly the same as those used in the example 2. The A-scope CRT pattern by those two transducers are shown in FIG. 4A and FIG. 4B. FIG. 4A is the result obtained by 5C10ILF20 and FIG. 4B is that by 4B10ILF. The ultrasonic flaw detecting conditions which gave the above-illustrated A-scope CRT patterns and the value of signal-to-noise-ratio which were measured at the same flaw detecting arrangements are shown in Table 3.

TABLE 3

| Transducer | 5C10ILF20 | 4B10ILF |
| --- | --- | --- |
| Signal-to-noise-ratio (dB) | 18 | 14 |
| Gain-value (dB) | 42 | 28 |
| Refraction angle (degree) | 45 | 45 |
| Ultrasonic equipment | portable | portable |

From the result which is shown in FIGS. 4A and 4B, the following evaluation is obtained: When the test material is annealed, i.e. solution-treated, the signal-to-noise-ratio which is given by the customary narrow-band type line-focusing transducer [FIG. 4B] may be improved to such an extent that it makes automatic flaw detecting possible. It should be realized, however, that from the standpoint of resolution, the customary narrow-band type transducer still may not satisfy the objects of this invention, especially when the wall-thickness of the test material is small. When the broad-band high-damping and non-resonance type line-focusing transducer 5C10ILF20 [FIG. 4A] is used, sufficient signal-to-noise-ratio is attained with good stability and only in this case can the objects of this invention be accomplished.

FIG. 5 shows the comparison of stability in ultrasonic static detection of 10 mm length longitudinal reference U-notches in welds of austenitic stainless steel tubing for broad band and narrow band transducers, and FIG. 6 is the comparison of signal-to-noise-ratios in of the same ultrasonic static detection.

The comparative tests were carried out by the same flaw-detecting as that used for the above examples as shown in FIG. 1, but echo heights are shown by gain value (dB) adjusted to bring the echo heights up to 40% of the full scale of the longitudinal axis of the CRT.

In FIGS. 5 and 6, N is noise detected in flaw-neighbouring sound welds at the same beam path distance as that of flaw-signal (S) when the search unit has been displaced longitudinally along the tubing axis. $N_{max}$ is the maximum noise within flaw-neighboring sound welds passed by the acoustic beam at the same search unit arrangement as that for flaw-signal (S) detection.

From the data of $S/N_{max}$ shown in FIGS. 5 and 6, it is concluded that automatic flaw-detection can be effected with stability for 0.1 mm depth-longitudinal U notch (10 mm length) at the inner as well as outer surfaces of the tubing as annealed, for 0.3 mm depth—longitudinal U notch at the inner surface of tubing as annealed having a wall thickness less than 3 mm, and for 0.3 mm depth—longitudinal U notch at the inner as well as outer surface of tubing as welded notwithstanding the wall thickness thereof.

I claim:

1. An ultrasonic flaw-detection method for austentic alloy steel longitudinally welded pipe or tubing, in which method a shear wave angle beam is employed utilizing an incidence angle larger than the critical angle, making the refraction angle of longitudinal waves larger than 90 degrees, further comprising applying the shear angle beam using a focusing transducer made of lead niobate ceramic.

2. An ultrasonic flaw-detection method according to claim 1, wherein the focusing transducer is adjusted to focus at any point on the acoustic beam path between the beam incident point and half skip distance point in the pipe or tubing, where a skip distance is a distance from the incident point of the beam on an outer surface of the pipe or tubing to a point where the beam having entered the thickness of the pipe or tubing again reaches the outer surface thereof after being once totally reflected by an inner surface of the pipe or tubing.

3. An ultrasonic flaw-detection method for austentic alloy steel longitudinally welded pipe or tubing, in which method a shear wave angle beam is employed utilizing an incidence angle larger than the critical angle, making the refraction angle of longitudinal waves larger than 90 degrees, further comprising applying the shear wave angle beam using a focusing transducer made of lead titanate ceramic.

4. An ultrasonic flaw-detection method according to claim 3, wherein the focusing transducer is adjusted to focus at any point on the acoustic beam path between the beam incident point and half skip distance point in the pipe or tubing, where a skip distance is the distance from the incident point of the beam on an outer surface of the pipe or tubing to a point where the beam having entered the thickness of the pipe or tubing again reaches the outer surface after being once totally reflected by an inner surface of the pipe or tubing.

* * * * *